United States Patent [19]

Bernstein

[11] Patent Number: 5,419,316
[45] Date of Patent: May 30, 1995

[54] ANESTHESIA EVAPORATORS

[76] Inventor: Jerome Bernstein, 10 Truman Ct., Middletown, N.Y. 10940

[21] Appl. No.: 925,266

[22] Filed: Aug. 6, 1992

Related U.S. Application Data

[63] Continuation-in-part of Ser. No. 747,944, Aug. 21, 1991, abandoned.

[51] Int. Cl.$^6$ .............................................. A61M 15/00
[52] U.S. Cl. ............................ 128/203.12; 128/203.21; 128/203.25
[58] Field of Search ....................... 128/203.12, 203.21, 128/203.25

[56] References Cited

U.S. PATENT DOCUMENTS

| | | | |
|---|---|---|---|
| 802,339 | 10/1905 | De Trey . | |
| 968,306 | 8/1910 | Winderlich . | |
| 1,071,389 | 8/1913 | Blosser . | |
| 1,203,391 | 10/1916 | O'Donnell . | |
| 1,304,339 | 5/1919 | McGregor . | |
| 2,623,519 | 12/1952 | Cohen | 128/200.19 |
| 2,641,253 | 6/1953 | Engelder . | |
| 2,696,211 | 12/1954 | O'Gatty . | |
| 2,944,547 | 7/1960 | Ziherl et al. . | |
| 3,123,071 | 3/1964 | Felts . | |
| 3,565,133 | 2/1971 | Jones . | |
| 3,578,042 | 5/1971 | Breiling . | |
| 3,630,438 | 12/1971 | Bickford | 128/203.14 |
| 3,874,381 | 4/1975 | Baum . | |
| 4,770,168 | 9/1988 | Rusz et al. | 128/203.12 |
| 4,825,860 | 5/1989 | Falb et al. | 128/203.12 |
| 4,867,212 | 9/1989 | Mohr et al. | 128/200.14 |
| 4,883,049 | 11/1989 | McDonald | 128/202.22 |

OTHER PUBLICATIONS

"Dräger Vapor 19.3/Vapor 19.2 for precision anesthetic metering independent of flow", Oct. 1984, Drägerwerk Ag Lübeck.

Primary Examiner—Edgar S. Burr
Assistant Examiner—Aaron J. Lewis
Attorney, Agent, or Firm—Philip Furgang

[57] ABSTRACT

Anesthetic agent positioning and conduit means are provided for anesthesia evaporators to position prepackaged, anesthetic agents, with respect to the anesthesia evaporator and to facilitate movement of the anesthetic agent from its package when so positioned and to conduct the anesthetic agent to a chamber within the evaporator for mixing with carrier gases and passage from the evaporator for anesthesia uses. In one embodiment the anesthetic agent is packaged in a bottle with an externally threaded neck and sealed by a membrane which, upon the bottle being threaded into a well carried by the evaporator, is severed by a spear-headed cutter disposed in the well that enables the anesthetic agent to pass from the bottle to the chamber. Fluid introduction means is provided in a modification to move air into the bottle and facilitate passage of anesthetic agent therefrom. In another embodiment the anesthetic agent is in a rectangular foil wrapped package that is received in a package receiver carried by the evaporator. Piercing members pierce the foil at several locations to permit the anesthetic agent to flow from the package and in one embodiment to also permit air to enter the package to facilitate such flow. A conduct conducts the anesthetic agent to the chamber in the evaporator. In a third embodiment a door is provided to permit entry into the anesthetic agent chamber and the anesthetic agent is in a cryogenically frozen block which when placed in the chamber of the evaporator sublimes on its own due to ambient temperatures or upon application of heat thereabout. In another embodiment the pre-packaged anesthetic agent is disposed at an angle of twenty degrees to the vertical; and in yet another embodiment the pre-packaged anesthetic agent container is connected to the evaporator is a first disposition and then moved to another disposition to permit flow of the anesthetic agent to the evaporator.

22 Claims, 4 Drawing Sheets

ANESTHESIA EVAPORATORS

This application is a Continuation-in-part of an earlier filed application Ser. No. 07/747,944 filed Aug. 21, 1991, now abandoned, and title "Anesthesia Evaporators."

BACKGROUND OF THE INVENTION-FIELD OF APPLICATION

This invention relates to anesthesia evaporators or vaporizers; and more particularly to such anesthesia vaporizers or vaporators which facilitate the mixing of anesthetic agents with carrier gases to facilitate delivery of anesthesia in appropriate anesthetizing proportions to patients.

BACKGROUND OF THE INVENTION-DESCRIPTION OF THE PRIOR ART

The delivery of anesthesia to a patient, to anesthetize the patient to facilitate performing an operation on the patient or to facilitate performing a medical procedure on the patient, has and can be accomplished in many ways and with many types of apparatus utilized for such purposes. Devices for presentation to a person of a substance, usually a gas, to be inhaled have existed for some time as shown, by way of example in U.S. Pat. No. 1,071,389 granted on Aug. 26, 1913 to J. W. Blosser for "Vaporizer And Inhaler" and in U.S. Pat. No. 1,304,339 granted on May 20, 1919 to R. R. McGregor for "Eucathol Inspirator." However, such devices merely pass air over a medicinal substance, with and without the application of heat respectively, and are not suitable to mix carrier gases and anesthetizing agents for delivery of anesthesia to a patient in an operating room.

Some early devices for providing anesthesia to a patient are shown and described in U.S. Pat. No. 802,339 granted on Oct. 17, 1905 to A. De Trey for "Inhaler" in U.S. Pat. No. 968,306 granted on Aug. 23, 1910 to W. J. Wunderlich for "Apparatus For Administering Anesthesia" and in U.S. Pat. No. 1,203,391 granted on Oct. 31, 1916 to P. S. O'Donnell for "Apparatus For Administering Gases And The Like Medicinal Agents." These devices are all substantially portable in construction and are also unsuitable for use in operating rooms and under conditions required by today's medical practice when performing operations and medical procedures. De Trey, for example, utilizes a glass capsule of anesthetic which must be broken in use and which further does not provide for safe disposition of the broken glass fragments which are inherently dangerous. O'Donnell also utilizes a capsule for the anesthetic and requires that capsule be placed within a holder that must be screwed together and constructed strong enough to function as a handle; which construction would require the loss of valuable time in an operating atmosphere and necessitate relatively fine hand and finger movement in the rush and tense environment of a medical operation or procedure. Wunderlich requires special disposition of an anesthetic agent receptacle with a lead cap through which a threaded tube must be inserted to acquire the anesthetic agent; or the use of a glass anesthetic agent capsule whose end must be broken in use. As stated earlier neither inherently dangerous glass fragments or screwing a tube into a lead cap are suitable for today's operating environments.

Other anesthesia administering devices are shown and described in U.S. Pat. No. 2,641,253 granted on Jun. 9, 1953 to A. E. Engelder for "Anesthesia Apparatus" and in U.S. Pat. No. 2,944,547 granted on Jul. 12, 1960 to F. A. Ziherl et al for "Portable Anesthesia Machine, Oxygen Inhalator And Resuscitator." However, Engelder's drip mask and Ziherl et al's portable device are both unsuitable for anesthesia delivery devices for today's operating room requirements. Similarly, the device shown and described in U.S. Pat. No. 3,123,071 granted on Mar. 3, 1964 to J. A. Felts FOR "Anesthetic Vaporizer" is unsuitable for operating room use because it only accepts liquid anesthetic from a syringe in syringe quantities; while devices, such as those shown and described in U.S. Pat. No. 4,770,168 granted on Sep. 13, 1988 to T. Rusz for "Electrically Controllable Anesthesia Vaporizer," are relatively complex and further add to the mass confusion and tense atmosphere in the operating room.

Other available anesthesia vaporizers, such as the "Drager Vapor 19" are shown and described at 1 Anesthesia 130 by R. D. Miller (Churchill Livingston, Inc., 1981) and by a vaporizer marketed under the name ENFLURATEC by Cyprane Ltd and a vaporizer for ethrane anesthetic marketed by Ohio Medical Products a division of Airco Inc of Madison Wis. But these units require the use of special tubes having first ends keyed to inlet ports of such vaporizers and second ends that are inserted into anesthetic agent containers and which are attached to such containers by internally threaded caps; or, alternatively, an internally threaded well to receive a bottle of anesthesia with its neck externally threaded. Such constructions are also awkward to use in the fast pace and crowded situations in an operating room because opening and dumping a bottle of anesthesia into a well while threading threads on the neck of the bottle into a receiver requires some dexterity and finite time and often results in spilling of the anesthetic agent and contamination of the air in the operating room that the operating room personnel must breath. On the other hand, finding a particular one or ones of a number of keyed tubes for fitting into and thereafter effecting the fit also requires dexterity in a relatively anxious environment. More importantly such action requires the availability of the right tube at the right time and that it be properly inserted in the right inlet receptacle. Furthermore, threading the cap provided at the other end of such tubes onto the threads of such anesthetic bottles also produces unacceptable spillage of anesthetic into the air within the operating room that the operating room personnel must breath.

SUMMARY OF THE INVENTION

It is therefore an object of this invention to provide new and novel anesthesia evaporators.

It is another object of this invention to provide new and novel mechanisms or devices to facilitate entry of anesthetic agents into anesthesia evaporators.

It is still another object of this invention to provide new and novel mechanisms or devices to introduce anesthetic agents, in premeasured packages, into anesthetic evaporators.

It is a further object of this invention to provide new and novel mechanisms or devices which accept prepackaged anesthetic agents wherein the package includes threaded elements which coact with threaded elements located on an anesthetic evaporator to seat the package of anesthetic agent prior to release of the anesthetic agent into the anesthetic evaporator.

It is yet a further object of this invention to provide new and novel mechanisms or devices which accept pre-packaged anesthetic agents wherein the package includes threaded elements which coact with threaded elements located on an anesthetic evaporator to seat the package of anesthetic agent and which disposes the anesthetic agent package at a predetermined angle to stabilize pressures.

It is still a further object of this invention to provide new and novel mechanisms or devices which accept pre-packaged anesthetic agents wherein the package includes threaded elements which coact with threaded elements located on an anesthetic evaporator such that the anesthetic agent package can be threadably connected to the evaporator in a first disposition of the anesthetic agent package and that the anesthetic agent package can thereafter be moved to a second disposition for passage of the anesthetic agent into the evaporator.

It is yet still a further object of this invention to provide new and novel mechanisms or devices to introduce prepackaged anesthetic agents into anesthetic evaporators wherein the anesthetic agent is prepackaged in foil that is opened when positioned for coaction with the anesthetic evaporator to facilitate introduction of the anesthetic agent into the anesthetic evaporator.

It is yet still another object of this invention to provide new and novel mechanisms or devices to introduce prepackaged anesthetic agents into anesthetic evaporators wherein the anesthetic agents are cryogenically frozen and introduced in that state into the anesthetic evaporator and thereafter sublime to release the anesthetic agent.

Other objects, features and advantages of the invention in its details of construction and arrangement of parts will be seen from the above and from the following description of the preferred embodiments when considered with the drawing and from the appended claims.

DESCRIPTION OF THE PREFERRED EMBODIMENT

Figures 1, 2, 3:
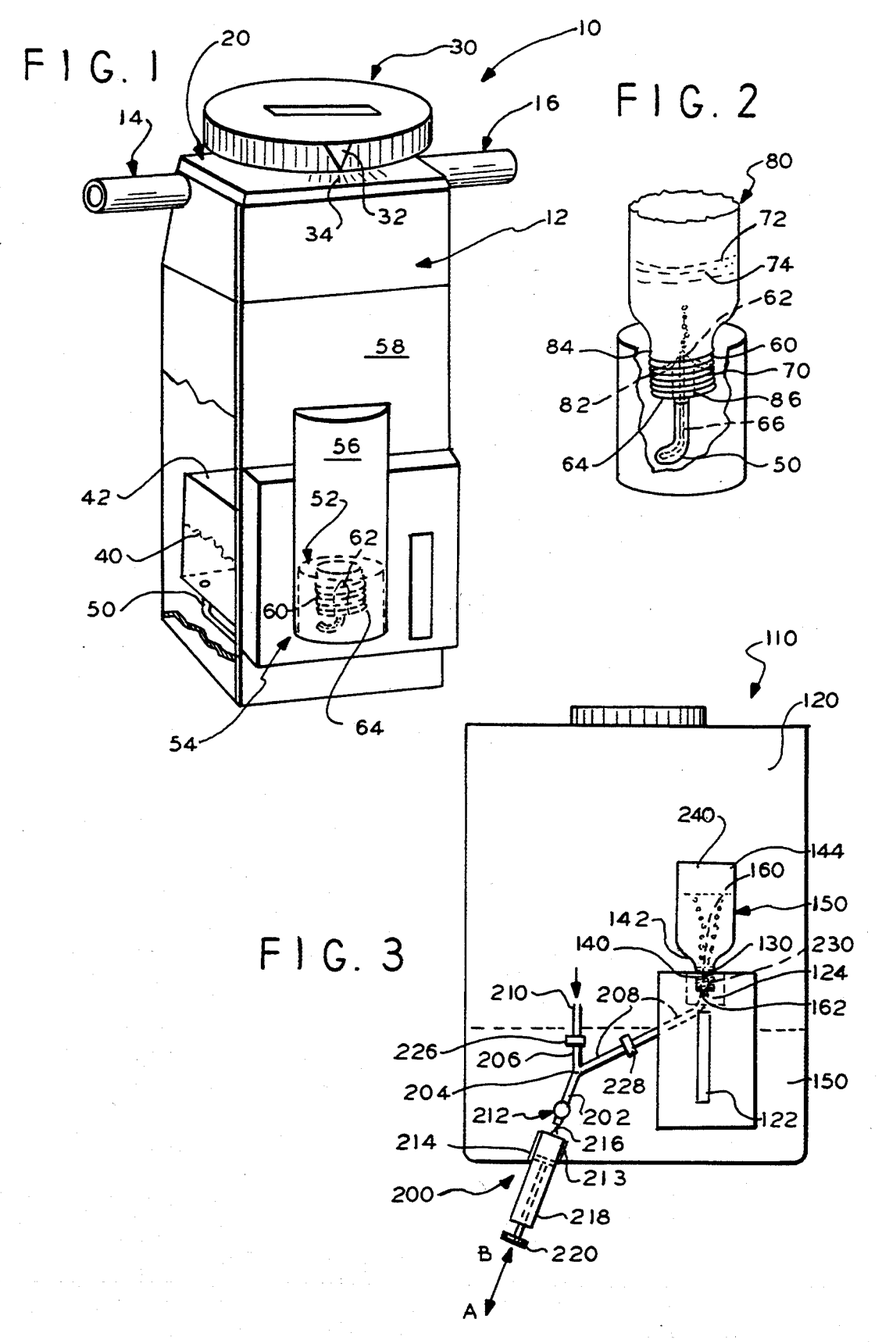
FIG. 1 is a perspective drawing of an anesthesia evaporator incorporating the instant invention.
FIG. 2 is a showing of the anesthetic agent introduction mechanism of the anesthesia evaporator of FIG. 1 enlarged to better show details thereof.
FIG. 3 is a schematic of a modified embodiment of the anesthetic agent introduction mechanism of FIG. 2 for use with the anesthesia evaporator of FIG. 1.

With reference to FIG. 1 there is generally shown at 10 an anesthesia evaporator including a body 12 which while schematically shown to be generally rectangular in cross section might just as well be square, round or any other convenient configuration. An inlet tube 14 and an outlet tube 16 extend from body 12 proximate its top 20. Tubes 14, 16 conduct carrier gases, such as oxygen or nitrous-oxide mixture, to and through vaporizer 10 and into proximity to pick-up and mix with an anaesthetic agent such as enflurane, halothane, isoflurane and any other commonly now or hereinafter used anesthetic agents. The mixing of the anesthetic agent and carrier gas is accomplished in a substantially conventional manner with the amount of anaesthetic agent to be picked up or mixed with the carrier gas controlled by a control knob 30 disposed on top of top 20 of body 12. A pointer 32 coacts with a scale 34 to indicate the percent of the mixture. An anaesthetic agent 40, generally in liquid form is disposed in an anaesthetic agent chamber 42 (FIGS. 1 and 2) positioned within body 12 with the interaction between anaesthetic agent 40 and the carrier gases taking place in a substantially conventional manner.

Anesthetic agent 40 travels into chamber 42 by way of a tube 50 extending between chamber 42 and an anaesthetic agent well 52 disposed at the base 54 of a depression 56 formed in the face 58 of body 12. Well 52 includes a set of internal screw threads 60 and a bladelike spear-head membrane cutter 62 extending up from a base 64 of well 52. An air tube 66 (FIG. 2) extends up through spear-head 62 and through tube 50 and has its other end (not shown) open to atmosphere.

Threads 60 are sized, shaped and configured to receive and coact with mating threads 70 (FIG. 2) on a pre-packaged anesthetic agent 72 utilized with and for evaporator 10. In this instance anesthetic agent 72 is in the form of a liquid 74 and is of the type generally and conventionally used as an anesthetic agent. Agent 72 is pre-packaged into a container in the form of a bottle 80 with an agent sealing membrane 82 disposed inside neck 84 of bottle 80 at approximately the level of anesthetic agent 72 therein but below the level of the tip 86 of neck 84 of bottle 80.

The relationship of agent sealing membrane 82 to tip 86 of neck 84 of bottle 80 is such that threads 70 of bottle 80 may be mated to and coact with threads 60 of well 52 until the respective threads 60, 70 are almost fully mated and tip 86 of neck 84 of bottle 80 almost fully seated in well 52. Further threading of threads 60, 70 to fully seat bottle in well 52 causes spear-head membrane cutter 62 to sever membrane 82 and permit anaesthetic agent 72 to spill into well 52, travel through tube 50, and into anaesthetic agent chamber 42 of evaporator 10.

Air tube 66 permits air to enter bottle 80 through spear-head 62 to facilitate passage of anaesthetic agent 72 from bottle 80.

While bottle 80 has been shown to be round it may just as well be any other convenient configuration as long as its neck is sized to facilitate threading into well 52. Furthermore, while neck 84 of bottle 80 and well 52 are respectively provided with continuous screw threads they may just as easily be provided with discontinuous threads or for that matter any other mating-type positioning and securing members as long as the package for the anaesthetic agent is well received and positioned within well 52 before the membrane releasing the anaesthetic agent is severed. Bottle or package 80 may be provided with an internally threaded cap to seal neck 84 and/or with another membrane at or proximate tip 86 of bottle 84 to further seal neck 84 and secure the inside thereof against contamination.

Should it be desired to have a particular anesthesia evaporator 10 be specific for a particular specific anesthetic agent such that is accomplished by forming threads 60 in well 52 and threads 70 on neck 84 of anaesthetic package 80 of a peculiar size, shape and configuration so that they only mate with each other. As such the threads on a package of anesthetic agent not specific for use with evaporator 10 will not be received by threads 60 in well 52 and the non-specific anesthetic agent will not be able to be used with that particular evaporator 10.

In FIG. 3 there is generally shown, in schematic, an anesthesia evaporator or vaporator 110 which includes an anesthetic agent chamber 120 disposed substantially similar to chamber 42 of evaporator 10 of FIGS. 1 and 2 and for the same purposes. A tube 122 has one of its ends disposed in chamber 120 and the other of its ends connected to a well 124 disposed, like well 50 of evaporator 10 of FIGS. 1 and 2, on a front wall of evaporator 10, to direct anesthetic agent from well 124 to chamber 120. Internal threads 130 are formed within well 124 of a size, configuration and disposition to coact with mating threads 140 formed on the outside of a neck 142 of an anesthetic agent package, in the form of a bottle 144, that is filled with an anesthetic agent 150. The coaction between threads 140 of bottle 144 and threads 130 of well 124 is the same as that described for similar elements of the FIG. 1 embodiment such that a spear-head membrane cutter 160, disposed within well 124, severs membrane 162 disposed within bottle 144 and permits anesthetic agent 150 to flow into well 124 and therefrom through tube 122 into chamber 120 as for the FIG. 1 embodiment.

An air supply assembly 200 is provided for evaporator 110 to facilitate the passage of anesthetic agent 150 from bottle 144 to chamber 120. A first fluid passage 202 connects at a "Y" joint 204 with a second fluid passage 206 and a third fluid passage 208. Passage 206 terminates at an end 210 disposed above the level of anesthetic agent 150 in chamber 120 while passage 208 extends up through spear-head membrane cutter 162.

A first valve 212 is disposed in passage 202, between a syringe receptacle 214 and "Y" joint 204, and is configured to be in open condition when a needle 216 at the end of a syringe 218 is inserted therethrough and in closed configuration when the syringe 218 is removed. A plunger 220 is provided for syringe 218. A check valve 226 is disposed in passage 206 and is configured to direct flow downward from above the surface of anesthetic agent 150. A check valve 228 is disposed in passage 208 and is configured to direct flow upward from syringe 218 through passage 208 through ports 230 in spear-head 162.

Thus by withdrawing plunger 220 (i.e. moving plunger 220 in the direction of arrow A-FIG. 3) fluid is drawn into passage 206 through valves 226 and 212 and into syringe 218. Movement of plunger 220 in the direction of arrow B (FIG. 3) forces such fluid back through passage 202 and into passage 208 then through check valve 228 and the rest of passage 208 and then out through ports 230 to bubble up through anesthetic agent 150 in bottle 144. An increase of air pressure in the bottle 144, and, upon withdrawing the plunger 220 a reduction of pressure facilitates the transfer of the agent from the bottle 144 to prevent air lock to facilitate movement of anesthetic agent 150 directly into chamber 120. The fluid thus used to facilitate emptying of anesthetic agent 150 from bottle 144 is the mixture of carrier gas and anesthetic agent.

Figure 4:
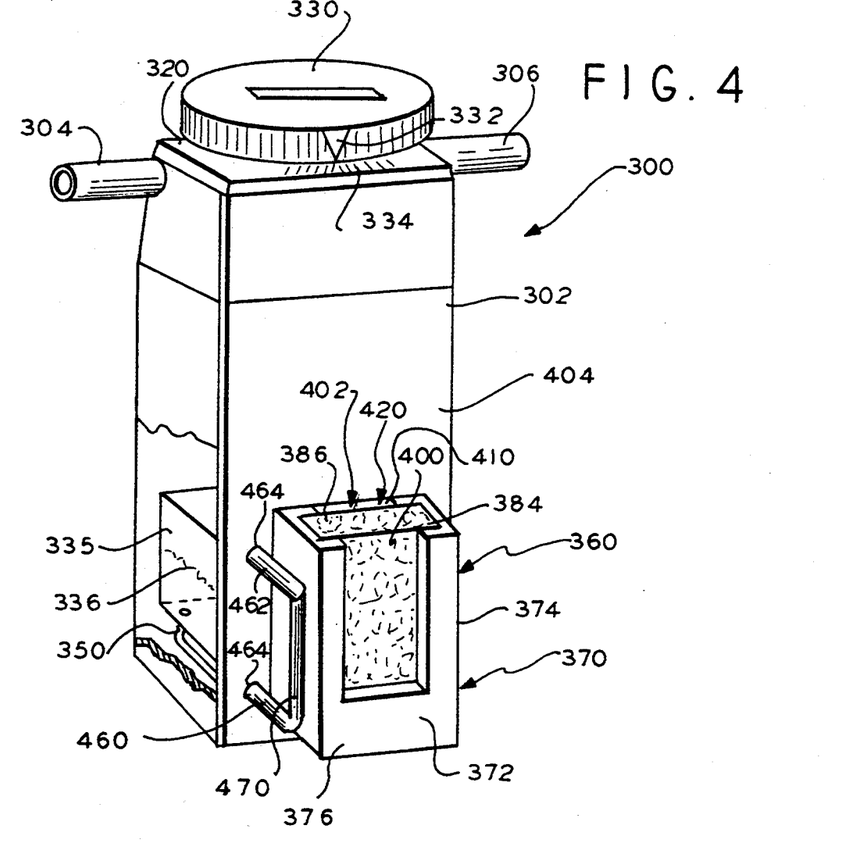
FIG. 4 is an isometric sketch of another alternative embodiment of anesthetic agent introduction mechanism, incorporating the instant invention, for use with anesthesia evaporators.

In the embodiment of FIG. 4 there is shown an anesthesia evaporator or vaporizer 300, like evaporator 10 of FIGS. 1 and 2, and which includes a body 302, inlet tube 304, outlet tube 306, top 320, control knob 330, pointer 332, scale 334 and anesthetic agent chamber 334 disposed to receive an anesthetic agent 336; all similar to like members described for the FIG. 1 embodiment and which all function and coact together as described for evaporator 10 of the FIG. 1 embodiment.

Figure 5:
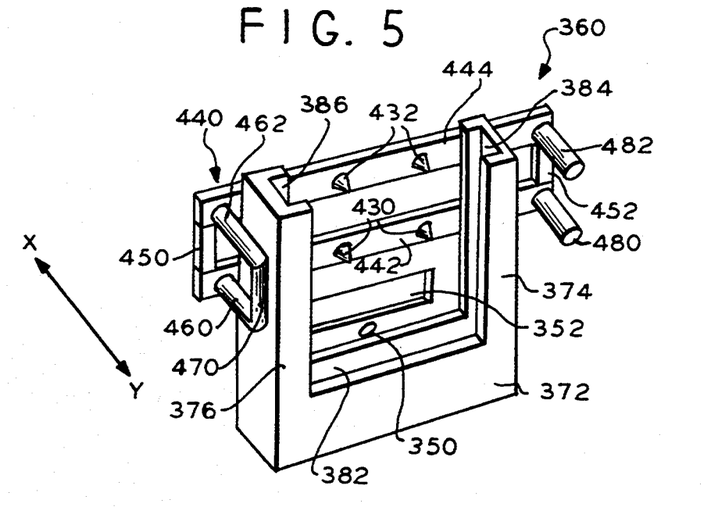
FIG. 5 is an enlarged sketch of the anesthetic agent package receiving, retention and opening mechanism for the anesthesia evaporator of FIG. 4; removed therefrom to better show details thereof.

A flow tube 350 extends from chamber 334 into an anesthetic agent well 352 (FIG. 5) which is carried by an anesthetic agent introduction mechanism 360 (FIGS. 4 and 5). An anesthetic agent package receptacle 370 carries well 352 and includes a bottom rail 372 and a pair of spaced side rails 374, 376 extending upwardly therefrom each formed to provide a track 382, 384, 386 respectively. Tracks 382, 384 and 386 are of a size, disposition and configuration to position a package 400 (FIG. 4) of anesthetic agent 336 proximate an opening 402 formed through a front face 404 of evaporator 300.

Package 400 is formed of foil of sufficient strength size and configuration to contain a pre-measured quantity of anesthetic agent 336 and for a snug fit in tracks 382, 384 and 386. If desired suitable gasketing may be provided within tracks 382, 384, 386 and at 410 on face 404 of evaporator 300.

An inner face 420 (FIG. 4) of foil package 400 is formed to be pierced by relatively sharp points 430 (FIG. 5) and 432 of a piercing device 440. A first bar 442 of piercing device 440 carries points 430 at a relatively low disposition with respect to package receptacle 370 and a package 400 when carried thereby. While a second bar 444 carries points 432 at a relatively high disposition with respect to package receptacle 370 and a package 400 when carried thereby. A pair of end bars 450, 452 position bars 442 and 444 in relative disposition with respect to each other, and all of such members within chamber 334 of evaporator 300.

A pair of operating rods 460, 462 (FIGS. 4 and 5) extend out respectively from bars 442, 444 (FIG. 5) proximate end bar 450, and through openings 464 (FIG. 4) formed through face 404 of evaporator 300 to have their ends connected by an operating handle 470. A pair of guide rods 480, 482 (FIG. 5) extend out respectively from bars 442, 444 proximate end bar 452 and through openings (not shown) formed through face 404 of evaporator 300 to coact with rods 460, 462 to guide the movement of points 430 and 432, in the directions of arrows X and Y (FIG. 5), between a removed position wherein points 430, 432 are spaced from inner face 420 of package 400 and a piercing position wherein points 430, 432 pierce inner face 420 of package 400.

When using evaporator or vaporizer 300 one need only connect suitable carrier gas conduits to inlet 304 and outlet 306 and thereafter place a foil package 400 of suitable anesthetic agent 336 in package receptacle 370 while piercing device 440 is positioned in its removed position so that its points 430, 432 are disposed away from interference with insertion of package 400 in receptacle 370. The operator then grips handle 470 and moves piercing device 440 in the direction of arrow Y (FIG. 5) moving points 430, 432 through inner face 420 of foil package 400. Movement of handle 470 and of piercing device 440 in the direction of arrow X (FIG. 5) pulls points 430, 432 out from inner face 420 of foil package 400.

The disposition of points 430 is such as to pierce inner face 420 of foil package 400 relatively low down when package 400 is disposed in receptacle 370 to facilitate spillage of anesthetic agent 336 therefrom into well 352 and therefrom through tube 350 into chamber 334. The disposition of points 432 is such as to pierce inner face 420 of foil package 400 relatively high up when package 400 is disposed in receptacle 370 and further facilitates the flow of anesthetic agent 336 from package 400. The sizing of package 400 and of tracks 382, 384, 386 of receptacle 370 is such as to provide a fluid tight fit of package 400 against front face 404 of evaporator 300 to prevent seepage of anesthetic agent 336. If desired the sizing of tracks 382, 384 and 386 and of package 400 can be selected to restrict evaporator 300 to a particular anesthetic agent or class of such agents.

Figures 6, 7:
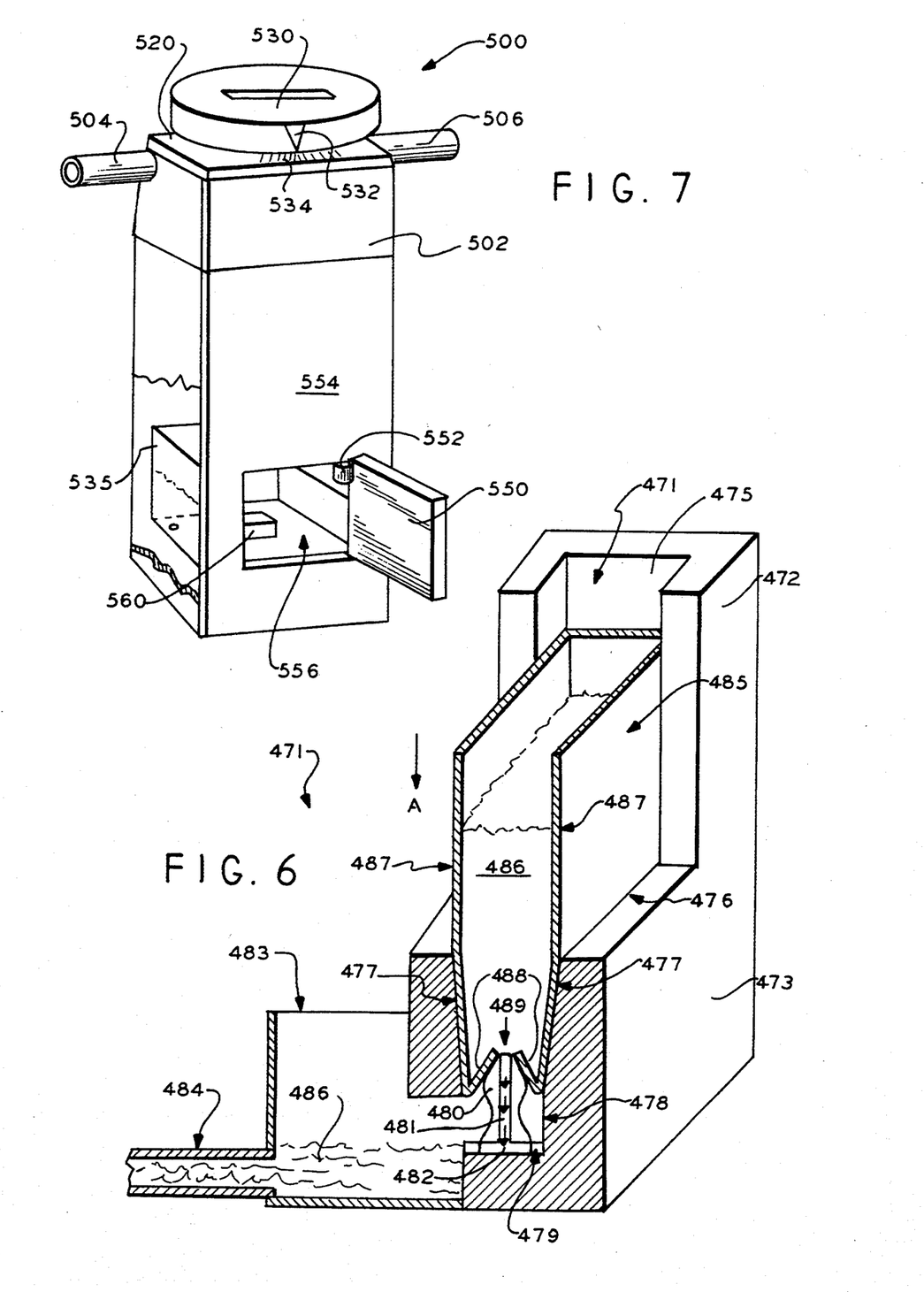
FIG. 6 is an isometric sketch in vertical section, of an alternative embodiment of anesthetic agent package receiving, retention and opening mechanism, incorporating the instant invention, for the anesthesia evaporator of FIG. 4, removed therefrom and enlarged to better show details thereof.
FIG. 7 is an isometric sketch of yet another alternative embodiment of anesthetic agent package receiving mechanism, incorporating the instant invention, for an anesthesia evaporator.

FIG. 6 shows at 471 an alternative construction for the anesthetic agent package receiving, retention and opening mechanism, or anesthetic agent introduction mechanism, 360 of FIG. 5. A pair of spaced side rails 472 (only one shown) extend upwardly from a bottom rail 473 and together form a substantially "U" shaped anesthetic package receiving and retention device open at its top 474. A package receiving track 475, formed in each side rail 472, extends up from a package receiving track 476 formed in bottom rail 473. Side walls 477 of track 476 taper inwardly and down and then terminate at lower sections 478 which may be vertical or continue to taper but which terminates at a floor 479 of track 476.

A plurality of spear-head membrane cutters 480 (only one shown) are disposed along and rise up from floor 479 of track 476. Cutters 480 are similar in construction to membrane cutters 62 of the FIGS. 1 and 2 embodiment or cutter 162 of the FIG. 3 embodiment except that a fluid passageway 481 extends down through spear-head membrane cutter 480 intersecting a fluid passageway 482 at the base thereof. An anesthetic agent well 483 is carried by and secured to the anesthetic receiving and retention device to receive fluid flow from passageways 481, 482 and otherwise from fluid flow about cutters 480 as will be hereinafter described. A conduit of flow tube 484 leads from well 483 to an anesthetic agent chamber (not shown) similar in construction and use to anesthetic agent chamber 334 of FIG. 4.

Tracks 475, 476 and mechanism 471 are of a size, configuration and construction to snugly receive a foil wrapped package 485 of anesthetic agent 486 similar to package 400 of the FIG. 4 embodiment. As package 485 is slid through top 474 of tracks 475, 476 in the direction of arrow A sides 487 of package 485 engage inner surfaces of tracks 475 and thereafter inner surfaces of track 476. Further movement of anesthetic agent package 485 into mechanism 471 results in coaction of sides 487 of package 485 with inwardly tapered side walls 477 of track 476 to securely grip and somewhat squeeze the bottom of package 485. The inward taper of side walls 477 is shown somewhat exaggerated to better show its details. The configuration of the taper of side walls 477 is such as to effect a grip on package sides 487 to facilitate severing of a bottom wall 488 of package 485 at 489, at each cutter and possibly in between to permit anesthetic agent 486 to flow out of package 485 and out through passages 481 of cutters 480 and down about the surfaces thereof onto floor 479 of track 476 and into well 483, flow tube 484 and therefrom to the anesthetic agent chamber to be utilized as described for the other embodiments.

The coaction of sides 487 of package 485 with side walls 477 of track 476 is also such that anesthetic agent 486, released by severance of bottom wall 488 of package 485, will not seep up around package 485.

In FIG. 7 there is generally shown at 500 an anesthesia evaporator or vaporizer quite similar in construction and function to evaporator 10 of FIG. 1 and evaporator 300 of FIG. 4. Evaporator 500 includes a body 502, inlet tube 504, outlet tube 506, top 520, control knob 530, points 532, scale 534, and anesthetic agent chamber 534; all substantially similar to like members described for the FIG. 1 and FIG. 4 embodiments and which function and coact together as described for those embodiments.

An access door 550 is hingedly connected at 552 to a front wall 554 of body 502 to provide access into chamber 534 through an opening 556 through front wall 554 and to close opening 556 and thereby access into chamber 534. Chamber 534 is of a size, disposition and configuration to receive package 560 of anesthetic agent.

The anesthetic agent within package 560 has been cryogenically frozen and is placed within chamber 534 while in its frozen state. Thereafter either holes are pierced through the skin of package 560 by a suitably pointed instrument, or package 560 is unwrapped fully or partially and the moiety within package 560 permitted to sublime so that the fluidic gas so produced mixes with carrier gases passing through evaporator 500 to provide appropriate anesthesia to a patient undergoing an operation or medical procedure. If desired a suitable heating element may be disposed proximate chamber 534 to facilitate, aid and if need be induce sublimation of the cryogenically frozen anesthetic agent in package 560. In the alternative, there may be provided a drawer (not shown) into which frozen anesthetic agent may be placed and inserted into chambers 534. The drawer upon closing, like two doors, seals the chamber from the outside.

Figure 8:
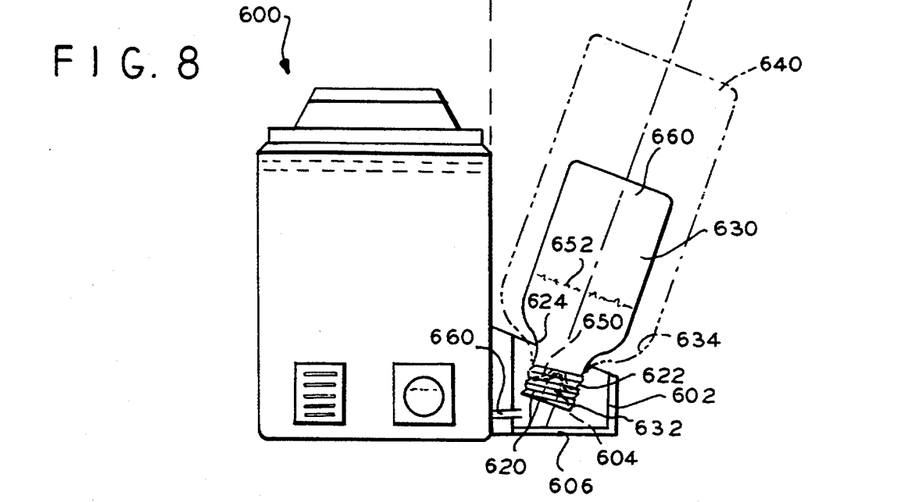
FIG. 8 is a schematic of a modified embodiment of anesthesia evaporator incorporating the instant invention.

In the embodiment of FIG. 8 there is generally shown at 600 an anesthetic evaporator or vaporizer of the type previously described and which includes an anesthesia agent well 602 which incorporates a blade-like membrane cutter 604 rising up from a base 606 of well 602. A set of internal threads 620 are provided within well 602 for coaction with external threads 622 formed about the neck 624 of an anesthetic agent package or container 630 in the form of a bottle. Bottle 630 is of the type and size for holding an anesthetic agent such as "Isoflurane." Threads 620 are also sized and disposed to coact with external threads 632 formed about the neck 634 a different size anesthetic agent package or container 640 (shown in phantom in FIG. 8). Bottle 640 is of a size and configuration for holding an anesthetic agent such as "Enflurane." Evaporator 10 and anesthetic agent packages 630 and 640 are similar to evaporator 10 and anesthetic agent package 72 of the FIG. 1 embodiment; except that anesthetic agent well 602 and its internal threads 620 and its membrane cutter 604 are disposed at an angle "X" to the vertical.

Thus, when the pre-packaged anesthetic agent in its package or container 630 (or 640) is threaded in place in well 602 membrane cutter 604 will sever the membrane 650 generally provided within bottle 630 (or 640) just as bottle 630 seats in well 602. Anesthetic agent 652 will flow from bottle 630 (or 640) into well 602 and from well 602 through a passage or tube 660 formed therein and into evaporator 600 for use thereby in an otherwise conventional manner.

Angle "X" is selected to be a 20 degrees to the vertical but angles acute to the vertical, preferably between 20 and 30 degrees to the vertical, will do. The angle so selected acts to dispose anesthetic package or container 630 (or 640) at an angle and functions to compensate and stabilize pressure on the anesthetic agent 652, as it enters evaporator 600, and to facilitate the passage of air through anesthetic agent 652 into an air space 660 within package or container 630 (640) to further facilitate flow of anesthetic agent 652 into evaporator 600.

Figures 9, 10:
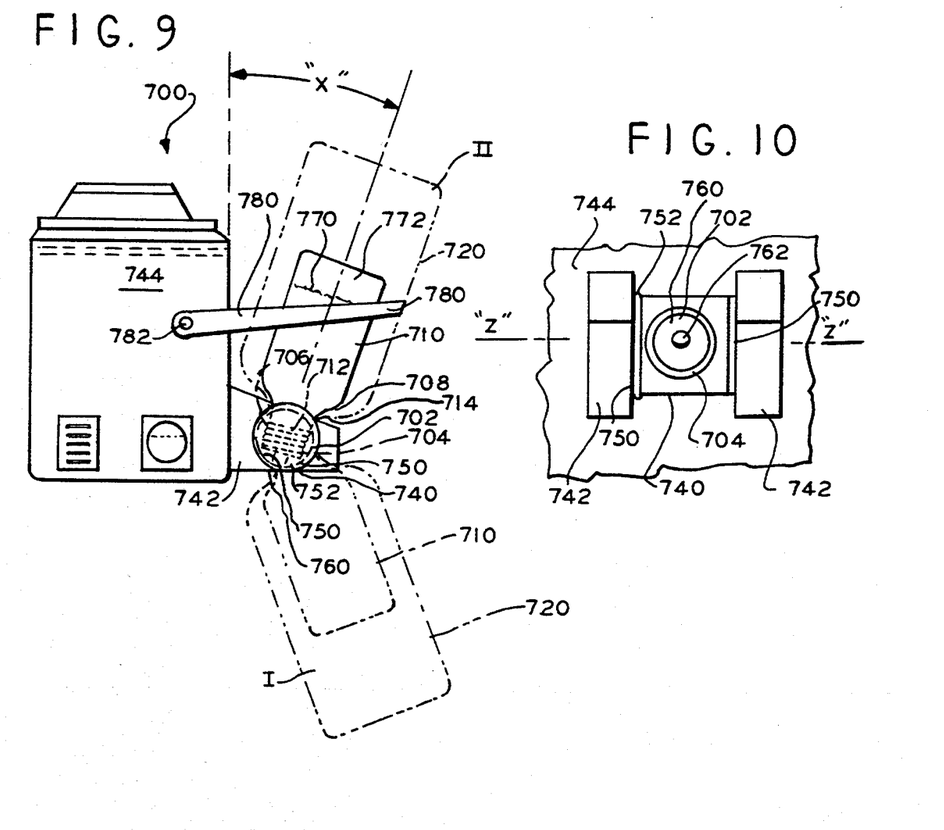
FIG. 9 is a schematic of another modified embodiment of anesthesia evaporator incorporating the instant invention.
FIG. 10 is an enlarged showing of a portion of the anesthesia evaporator of FIG. 9 to better show details thereof.

In the embodiment of FIGS. 9 and 10 there is generally shown at 700 an anesthetic evaporator or vaporizer of the type previously described and which includes an anesthesia agent well 702 which incorporates a set of internal threads 704 disposed for coaction with external threads 706 formed about the neck 708 of an anesthetic agent package or container 710 in the form of a bottle. Bottle 710 is of the type and size for holding an anesthetic agent such as "Isoflurane." Threads 706 are also sized and disposed to coact with external threads 712 formed about the neck 714 a different size anesthetic agent package or container 720 (shown in phantom in FIG. 8). Bottle 720 is of a size and configuration for holding an anesthetic agent such as "Enflurane." Evaporator 10 and anesthetic agent packages 710 and 720 are similar to evaporator 600 and anesthetic agent packages 630, 640 of the FIG. 8 embodiment; except that anesthetic agent well 702 and its internal threads 704 are disposed in a generally cylindrical member 740 rotatably carried by a pair of arms 742 that extend out from a wall 744 of evaporator 700. Cylindrical member 740 is carried by arms 742 for rotation about an axis of rotation "Z" (FIG. 10) between a loading position "I" (FIG. 9) and an operative or discharge position "II". A cylinder seat 750 is formed in each arm 742 and so as to face each other to receive therebetween cylindrical member 740. An "O" ring 752 is disposed in at least one of said cylinder seats 750; but, if desired, "O" rings 752 may be disposed in each seat 750. "O" ring(s) 752 apply pressure on cylindrical member 740 in the horizontal direction (along the direction of axis "Z" (FIG. 10) sufficient to retain cylinder member 740 in desired selected positions but such as to permit selected rotation of cylinder member 740 between its positions I and II as will be hereinafter described.

Base 760 of well 702 is formed with an opening 762 which communicated with a passage into evaporator 700 and which receives anesthetic agent 770 from bottle 710 (or 720) and directs agent 770 through that passage into evaporator 700 for use in conventional manner. Alternatively, a nozzle or tube end may extend up from opening 762 but need not enter the bottle 720 or 710.

The anesthetic agent container 710 (or 720) need not contain a membrane 650 because the construction of the invention of FIGS. 9 and 10 obviates the need of an anesthetic agent package with such a sealing membrane. In similar manner to that described above for the embodiment of FIG. 8 the disposition of bottle or package 710 (720) at the selected angle functions to compensate and stabilize pressure on anesthetic agent 770 and to facilitate its flow into evaporator 700.

In use the cap or cover provided for anesthetic agent package 710 (or 720) is removed and with cylindrical member 740 disposed to receive its anesthetic agent package 710 (or 720) in the I position. External threads 706 (or 712) of bottle 710 (or 720 respectively) are threaded into internal threads 704 of well 702 until bottle 710 (or 720) is fully seated in well 704. Bottle 710 (or 720) is then rotated, along with cylindrical member 740, into the II position and anesthetic agent 770 will pour into well 704 and tube end 762 and then into evaporator 700. Bottle 710 (and 720), like bottles 630 and 640 of the FIG. 8 embodiment, is preferably disposed at an angle "X" to the vertical to compensate and stabilize pressure upon anesthetic agent 770. Angle "X" is preferably selected at 20 degrees to the vertical but angles between 20 and 30 degrees to the vertical will also do.

If desired, a strap 780 (FIG. 9) may be connected by suitable connecting means 782 to evaporator 700 and disposed as shown in FIG. 9 to further secure bottle 710 (or 720) in its II or discharge position. A strap (not shown) like strap 780 may also be utilized with bottles 630, 640 of the FIG. 8 embodiment.

From the above description it will thus be seen that there has been provided new and novel anesthetic agent evaporators which are relatively simple and reliable in construction and operation.

It is understood that although I have shown the preferred embodiments of my invention that various modifications may be made in the details thereof without departing from the spirit as comprehended by the following claims.

What is claimed is:

1. An anesthesia evaporator; comprising:
  (a) body means housing carrier gas inlet and outlet passages and an anesthetic agent chamber disposed to receive an anesthetic agent and to present said anesthetic agent to carrier gases when passing therethrough to provide anesthesia and control means operative for effecting selected mixing of anesthetic agent and carrier gases;
  (b) anesthetic agent positioning and introduction means carried by said body means for positioning a pre-packaged, selected anesthetic agent with respect to said body means and for introducing anesthetic agent to said anesthetic agent chamber;
  (c) said anesthetic agent positioning and introduction means positioning a pre-packaged, selected anesthetic agent at a predetermined angle with respect to said body means;
  (d) at least a portion of said anesthetic agent positioning and introduction means being fabricated as a cylindrical member and disposed for rotation, about a cylindrical member axis of rotation, for movement between at least a first position and a second position; and
  (e) "O" ring means coacting with said cylindrical member to apply pressure to said cylindrical member to facilitate positioning said cylindrical member in either said first position or said second position while permitting movement of said cylindrical member between said first position and said second position;

(f) said cylindrical member of said anesthetic agent positioning and introduction means in said first position thereof being disposed to receive a pre-packaged anesthetic agent and in said second position thereof said cylindrical member and said pre-packed anesthetic agent are disposed to provide the anesthetic agent to the anesthetic evaporator.

2. The anesthesia evaporator of claim 1, wherein said second position will disposed the pre-packaged anesthetic agent at a predetermined angle.

3. The anesthesia evaporator of claim 2, wherein said predetermined angle is between twenty degrees and thirty degrees to the vertical.

4. The anesthesia evaporator of claim 3, wherein said predetermined angle is at twenty degrees to the vertical.

5. The anesthesia evaporator of claim 4, wherein strap means are carried by the anesthesia evaporator for coaction with the pre-packaged anesthesia agent to dispose same in said second position.

6. The anesthesia evaporator of claim 4, wherein the pre-packaged anesthetic agent need not be membrane sealed.

7. An anesthesia evaporator; comprising:
(a) body means housing carrier gas inlet and outlet passages and an anesthetic agent chamber disposed within said body means to receive an anesthetic agent and to present said anesthetic agent to carrier gases when passing therethrough to provide anesthesia and control means operative for effecting selected mixing of anesthetic agent and carrier gases;
(b) anesthetic agent positioning and introduction means carried by and external to said body means for positioning a pre-packaged, selected anesthetic agent with respect to said body means for introducing anesthetic agent to said anesthetic agent chamber;
(c) said anesthetic agent positioning and introduction means including an anesthetic well means carried by said body means and connected by fluid passage means to said anesthetic agent chamber;
(d) said well means including internal threaded package securing members;
(e) the anesthetic agent package including a bottle having a neck with external threaded package securing members
(f) said securing members of said well means and said securing members of the anesthetic agent package being peculiarly matched so that only selected anesthetic agent packages can be received by said well means;
(g) said anesthesia agent bottle including a severable sealing membrane disposed proximate said neck of said bottle and said well means including a membrane cutter disposed to sever said sealing membrane as the threaded members on said bottle and said threaded members in said well means are threaded together;
(h) said membrane cutter including fluid passage means to conduct fluid into an anesthetic package when disposed thereabout to facilitate passage of anesthetic agent therefrom; and
(i) fluid input means connected to said fluid passage means to introduce fluid thereinto;
(j) said fluid input means including first fluid passage means for conducting fluid from said anesthetic agent chamber to second fluid passage means and therefrom to an anesthetic package disposed at said well means.

8. The anesthesia evaporator of claim 7, including syringe means connected to said first and second fluid passage means to effect fluid movement therethrough and check valve means disposed in each of said first and second fluid passages to direct the flow of fluid therethrough.

9. An anesthesia evaporator; comprising:
(a) body means housing carrier gas inlet and outlet passages and an anesthetic agent chamber disposed within said body means to receive an anesthetic agent and to present said anesthetic agent to carrier gases when passing therethrough to provide anesthesia and control means operative for effecting selected mixing of anesthetic agent and carrier gases;
(b) anesthetic agent positioning and introduction means carried by and external to said body means for positioning a pre-packaged, selected anesthetic agent with respect to said body means for introducing anesthetic agent to said anesthetic agent chamber;
(c) said anesthetic agent positioning and introduction means including a frame like member disposed on said body means and defining an anesthetic package receiving space of predetermined size and configuration to position an anesthetic agent package of predetermined size and configuration proximate said body means;
(d) anesthetic agent package opening means disposed for coaction with a package of anesthetic agent when positioned in said anesthetic agent package receiving space; and
(e) anesthetic agent conduit means disposed to conduct anesthetic agent from said receiving space to said anesthetic agent chamber.

10. The anesthesia evaporator of claim 9, wherein the anesthetic agent package is membrane wrapped and said anesthetic agent package opening means comprise at least one pointed member movable between a first position engaging and severing the membrane of the anesthetic package and a second position removed therefrom to permit anesthetic agent to flow from the anesthetic agent package.

11. The anesthesia evaporator of claim 10, wherein there are a plurality of pointed members.

12. The anesthesia evaporator of claim 11, wherein some of said plurality of pointed members are disposed to pierce the anesthetic package membrane at relatively low positions when the package is disposed in said package receiving space and others of said plurality of pointed members are disposed to pierce the anesthetic membrane at relatively high positions when the package is disposed in said package receiving space.

13. The anesthesia evaporator of claim 12, wherein said predetermined configuration of the anesthetic package is rectangular and said membrane is foil.

14. The anesthesia evaporator of claim 9, wherein the anesthetic agent package is membrane wrapped and said anesthetic agent package opening means comprises at least one membrane cutter disposed to sever the membrane of an anesthetic agent package when positioned in said frame like member.

15. The anesthesia evaporator of claim 14, wherein said frame like member includes at least a pair of spaced sides and a bottom each including wall means disposed to receive an anesthetic agent package and tapering inwardly at a predetermined location to snugly receive and hold an anesthetic agent package when positioned therewithin.

16. The anesthesia evaporator of claim 15, wherein said membrane cutter is disposed and rises up from a bottom of said frame like member said membrane being foil.

17. The anesthesia evaporator of claim 16, wherein a fluid passageway is provided through said membrane cutter.

18. The anesthesia evaporator of claim 17, wherein there are a plurality of said membrane cutters.

19. An anesthesia evaporator; comprising:
(a) body means housing carrier gas inlet and outlet passages and an anesthetic agent chamber disposed to receive a pre-packaged, selected anesthetic agent in a cryogenically frozen state and to present said anesthetic agent to carrier gases when passing therethrough to provide anesthesia and control means operative for effecting selected mixing of anesthetic agent and carrier gases; and
(b) anesthetic agent positioning and introduction means carried by said body means for positioning the anesthetic agent with respect to said body means and for introducing the anesthetic agent to said anesthetic agent chamber;
(c) said anesthetic agent positioning and introduction means including an opening means formed through said body means to facilitate disposition of an anesthetic agent within said anesthetic agent chamber and closure means movable between an open position permitting access to said anesthetic agent chamber and a closed position restricting access to said anesthetic agent chamber;
(d) the anesthetic agent being in a covered package when placed in said anesthetic agent chamber and the covered package being at least partially opened when placed therein.

20. The anesthesia evaporator of claim 19, wherein the anesthetic agent, once placed within said anesthetic agent chamber is caused to sublime.

21. The anesthesia evaporator of claim 20, wherein heating means are provided within said body means to facilitate sublimation of the anesthetic agent when disposed therewithin.

22. An anesthesia evaporator; comprising:
(a) body means housing carrier gas inlet and outlet passages and an anesthetic agent chamber disposed within said body means to receive an anesthetic agent and to present said anesthetic agent to carrier gases when passing therethrough to provide anesthesia and control means operative for effecting selected mixing of anesthetic agent and carrier gases;
(b) anesthetic agent positioning and introduction means carried by and external to said body means for positioning a pre-packaged, selected anesthetic agent with respect to said body means for introducing anesthetic agent to said anesthetic agent chamber;
(c) said anesthetic agent positioning and introduction means positioning a pre-packaged, selected anesthetic agent at a predetermined angle with respect to said body means;
(d) at least a portion of said anesthetic agent positioning and introduction means being fabricated as a cylindrical member and disposed for rotation, about a cylindrical member axis of rotation, for movement between at least a first position and a second position; and
(e) "O" ring means coacting with said cylindrical member to apply pressure to said cylindrical member to facilitate positioning said cylindrical member in either said first position or said second position while permitting movement of said cylindrical member between said first position and said second position.

* * * * *